United States Patent
Simisker et al.

(10) Patent No.: US 7,183,088 B2
(45) Date of Patent: Feb. 27, 2007

(54) **THERMOPHILIC MICROORGANISM *BACILLUS COAGULANS* STRAIN SIM-T DSM 14043 FOR THE PRODUCTION OF L(+)-LACTATE FROM FERMENTABLE SUGARS AND THEIR MIXTURES**

(75) Inventors: Jaan Simisker, deceased, late of Tartu (EE); by Aida Simisker, legal representative, Tartu (EE); Allan Nurk, Tartu (EE); Ain Heinaru, Tartu (EE)

(73) Assignee: The University of Tartu, Tartu (EE)

( * ) Notice: Subject to any disclaimer, the term of this patent is extended or adjusted under 35 U.S.C. 154(b) by 13 days.

(21) Appl. No.: 10/471,514

(22) PCT Filed: Mar. 15, 2002

(86) PCT No.: PCT/EE02/00003

§ 371 (c)(1),
(2), (4) Date: Aug. 9, 2004

(87) PCT Pub. No.: WO02/074934

PCT Pub. Date: Sep. 26, 2002

(65) Prior Publication Data

US 2006/0040367 A1    Feb. 23, 2006

(30) Foreign Application Priority Data

Mar. 16, 2001  (EE) ................ 200100164

(51) Int. Cl.
*C12P 7/56*    (2006.01)

(52) U.S. Cl. ................ 435/139; 435/252.31; 435/170; 435/252.5

(58) Field of Classification Search ................ 435/139, 435/170, 252.31, 252.5
See application file for complete search history.

(56) References Cited

U.S. PATENT DOCUMENTS 3,697,378 A * 10/1972 Smalley ........................ 435/99
4,734,365 A *  3/1988 Haga et al. ................... 435/99
5,079,164 A     1/1992 Kirkovits et al.

FOREIGN PATENT DOCUMENTS

EP         354828 A1 *  2/1990
EP         0770684       5/1997
WO   WO 200277252 A1 * 10/2002

OTHER PUBLICATIONS

Payot, T., et al., "Lactic Acid Production by *Bacillus coagulans*-Kinetic Studies and Optimiazation of Culture Medium for Batch and Continuous Fermentations", Enzyme and Microbial Technology, vol. 24, No. 3/4, Feb. 1999, pp. 191-199.

Zayed, G., et al., "Batch and Continuous Production of Lactic Acid from Salt Whey Using Free and Immobilized Cultures of *Lactobacilli*", Appl. Microbiol. Biotechnol, vol. 44, 1995, pp. 362-366.

* cited by examiner

*Primary Examiner*—Leon B. Lankford, Jr.
*Assistant Examiner*—Susan E. Fernandez
(74) *Attorney, Agent, or Firm*—Reed Smith LLP

(57) ABSTRACT

Thermophilic microorganism *Bacillus coagulans* strain SIM-7 DSM 14043 for the production of L(+)-lactate from fermentable sugars, including dextrines and starch. The temperature of cultivation is 53–65° C. being the optimal. The final concentration of L(+)-lactate in fermentation is 12% with the yield of 95%. The cultivation of this strain of microorganism is possible without the high-temperature sterilization of equipment and media. Using cereal flour as the source of fermentable sugars, the need of the strain of the microorganism for mineral and nitrogen salts will be covered by the compounds present in the cereals.

5 Claims, No Drawings

THERMOPHILIC MICROORGANISM *BACILLUS COAGULANS* STRAIN SIM-T DSM 14043 FOR THE PRODUCTION OF L(+)-LACTATE FROM FERMENTABLE SUGARS AND THEIR MIXTURES

TECHNICAL FIELD

Invention belongs to the area of biotechnology and is usable for production of optically pure L(+)-lactate via microbiological synthesis.

BACKGROUND ART

Microbiological synthesis of L(+)-lactate is based on homolactic fermentation, resulting in two molecules of lactate from one molecule of hexose fermented (for example glucose or galactose).

Industrial chemical synthesis of pure L(+)-lactate is not resolved up to know, therefore there is no alternative to the microbiological synthesis of this compound.

In microbiological synthesis of L(+)-lactate, from the point of view of efficiency of energy consumption the maximum possible cultivation temperature of the microbial strain favouring set up the fermentation process without a high temperature sterilization steps of equipment and fermentation media is crucial.

In currently available processes based on *Lactobacillus* species the cultivation temperature does not exceed 45° C. that does not exclude contamination with thermophilic microorganisms if cultivation proceeds in rich nutrient media in nonsterile conditions. (J. H. Litchfield; In Advances in Applied Microbiology, Neidleman S. L. ed, Vol. 42, pp 45–95, 1996). The optimal cultivation temperature is 52° C. in processes based on *Bacillus coagulans* TB/04 (T. Payot, Z.Chemaly, F. Fick Enzyme and Microbial Technology, 24, pp 191–199). The disadvantage in this case is inhibition of the process at high concentrations of sugars (over 7,5%) complicating the use of this strain in industrial scale.

The prototype to the present invention is the microbial strain *Bacillus coagulans* DSM 5196. (U.S. Pat. No. 5,079, 164; C12P 7/56, C12R 1/07; Jungbunzlauer Aktiengesellschaft, 1992). In the processes based on this organism the optimum cultivation temperature is 52° C. It is possible to cultivate this organism at the initial concentration of sugars up to 20%. However, this organism can convert only 70% of glucose or sucrose of the growth media to lactate that is less than in current industrial applications (85–90%).

Furthermore, *Bacillus coagulans* DSM 5196 is not able to hydrolyse starch, dictating the need of preliminary treatment of the starch as a cheep raw material (liquefaction and saccharification) in the separate technological process.

DISCLOSURE OF INVENTION

The aim of the present invention is the thermophilic strain of microorganism, able to grow and produce lactate at higher temperature than described for analogous processes up to know, being more resistant to the high initial sugar concentrations, able to hydrolyse starch and suitable for the production of L(+)-lactate either from both fermentable monosaccharides and starch.

The object of the invention is a thermophilic strain of microorganism *Bacillus coagulans* SIM-7 DSM14043 that was isolated from overheated cereal (wheat) with the characteristics of microbial degradation. Wheat was milled and starch was liquefied. Resulting hydrolysate with the 18–20% content of sugar was used at 60° C. as an enrichment culture. The further selection of the microbial strain was achieved using standard microbiological methods.

Cultural and morphological characters. Colonies of the strain of microorganism *Bacillus coagulans* SIM-7 DSM 14043 are round umbonate, shiny, transparent, smooth surface, dry composition, and a diameter of 2 . . . 3 mm. Long gram-positive stick-shaped cells form chains. Cells are motile, form subterminal oval endospores.

Physiological and biochemical characters. The strain of microorganism grows on monosaccharides glucose, mannose, galactose, fructose and on disaccharides sucrose, maltose, cellobiose. From polysaccharides it grows on starch. Lactose is not fermented. It cannot degrade casein and gelatin.

It has fermentative metabolism. It ferments glucose and starch to L(+)-lactate without forming $CO_2$. Formation of D(−)-lactate is absent. Oxygen-tolerant. Catalase-positive and cytochrome c negative. Indole-forming ability is absent.

Growth temperature. The strain of microorganism grows at the temperature up to 65° C. and the viability of spores is retained at 85° C. at least during 40 minutes. Its optimal temperature of cultivation is 57° C. and it converts fermentable sugars, including starch, to the highly pure level of L(+)-lactate, the yield of which from the metabolised sugar reaches 95%. It is able to grow and produce L(+)-lactate at temperature up to 65° C. that is 5–10° C. higher than in the case of other strains reported earlier.

Identification of the strain of microorganism as the object of invention.

By using gram-positive microbial identification system of the company Biolog Inc. based on the pattern of metabolic activities (GP2 MicroPlate) the database GP Database (release 4.01A) the strain SIM-7 was identified with the highest probability (99%) as species *Bacillus thermoglucosidasius*. These data are, however, in contradiction with the 16S rRNA gene sequence data of the strain SIM-7 (Gene Bank acc. nr. AF346895). The gene bank data suggest the closest relatives of the SIM-7 strain the strain *Bacillus* sp HC15 (AC252329) with two differences, *Bacillus coagulans* NCDO 1761 (X60614) with six differences, *Bacillus coagulans* IAM 12463 (D16267) with seven differences and *Bacillus coagulans* JCM2257 (D8313) with eight differences of the 1464 nucleotides in total. At the same time, *Bacillus thermoglucosidasius* (ABO21197) differs in 131 nucleotides tested. Dr Watanabe et al. [Watanabe, K., Kitamura, K., Suzuki, Y (1996) Appl. Environ. Microbiol. 62:2066–2073] have compared nucleotide sequences of one catabolic gene, oligo-1, 6-glucosidase in strains *Bacillus thermoglucosidasius* KP1006 and *Bacillus coagulans* ATCC 7050. The overall sequence similarity of these proteins was 59% (Watanabe et.al.). Both the 16S rRNA gene sequence and the partial nucleotide sequence of the oligo-1,6-glucosidase gene of the strain SIM-7 clearly show its affiliation to the species *Bacillus coagulans*. Between the nucleotide positions 643 and 1287 of this gene of the strains *Bacillus coagulans* ATCC 7050 and *Bacillus coagulans* SIM-7 DSM 14043 there are only two differences, both leading to the exchange of the amino acid $Met_{399}$/Ile and $Gln_{402}$/His, correspondingly. (respective nucleotide sequences, GeneBank D78342, a in position 1244 instead of g and t in position 1253 instead of a). Consequently, the strain SIM-7 is a non-typical thermophilic variant of the species *Bacillus coagulans*, despite the general metabolic similarity to the species *Bacillus thermoglucosidasus*. The strain *Bacillus coagulans*

SIM-7 DSM 14043 also has no beta-galactosidase activity and differently from the strain *Bacillus coagulans* DSM 5196 (Kirkovits et al.) cannot grow on lactose but can grow on galactose.

The microorganism with the properties mentioned above was deposited in Deutsche Sammlung für Mikroorganismen und Zellkulturen GmbH, under the registration number DSM 14043, 08.02.2001.

The ability of the strain of microorganism to grow at a high temperature and use dextrines simplifies the production of lactate from starch, enabling to avoid saccharification of the starch as a separate technological step and thus saves glucoamylase needed for saccharification and makes the process cheaper.

In the fermentation of partially liquefied starch at the temperature 57° C. the energy for mixing decreases due to the lower viscosity of the medium. The ability to ferment several mono- and disaccharides makes the strain useful for the production of L(+)-lactate from the complex substrates of sugars or from the mixture of them. If cereals will be used as the source of starch the needs of the strain for the mineral and nitrogen compounds will be covered mostly by the compounds derived from the cereals. The strain of microorganism is resistant to high initial concentrations of sugars (17–20%) in growth medium, it accumulates glucose in the growth medium but accumulates 13–14% of calcium lactate in the medium. Thanks to the better solubility of calcium lactate at a higher temperature of fermentation, if the process involves $Ca^{2+}$ for neutralization, it is possible to elevate the concentration of calcium lactate up to 160–170 g $l^{-1}$.

Method for the production of L(+)-lactate from fermentable sugars and its mixtures is based on the cultivation of the strain of microorganism at the temperature range between 53–65° C., with the temperature optimum for cultivation 57° C. in media consisting partially fermentable sugars, including dextrines, starch and other nutrients. As the result of fermentation the final concentration of L(+)-lactate obtained is 12% with the yield of 95%. The cultivation of the strain of microorganism will be carried out without high temperature sterilization of equipment and medium. Using cereal flour as the source of sugars in fermentation, the needs of the strain of microorganism for the mineral and nitrogen compounds in growth media will be covered by compounds derived from the cereal.

DESCRIPTION OF EMBODIMENTS

1. Isolation of the Thermophilic Strain of Microorganism *Bacillus Coagulans* SIM-7 DSM 14043.

The strain of microorganism was isolated from overheated and with the characteristics of microbial degradation of cereal (wheat). Wheat mass was ground and liquefied. Resulting starch hydrolysate with the sugar content of 18–20% was used as a enrichment culture at the temperature 60° C. The culture was spread to the single colonies, the colonies with the ability to acidify the medium were picked up and were subsequently selected for homolactic fermentation ability by the absence of production of $CO_2$. The production of L(+)-lactate was enzymatically tested by L-lactate dehydrogenase. Among the thermotolerant, oxygen resistant and L(+)-lactate producing colonies the pure culture of *Bacillus coagulans* SIM-7 DSM 14043 was isolated.

2. Production of L(+)-Lactate

The *Triticale* flour (285 g) was suspended in 1 liter of water and the starch was liquefied with α-amylase at 85° C. up to DE=22,5. Liquefied starch was saccharafied with glucoamylase at 60° C. Non-soluble fibre material and protein were separated from saccharafied starch by centrifugation. To the pasteorized supernatant with glucose content of 14,8 g l-1up to 0,6% of yeast extract was added and used as a fermentation medium for *Bacillus coagulans* SIM-7 DSM 14043. The lactic acid formed was neutralized with the calcium carbonate added to the fermentation media. The pH of the fermentation was between 5,3–6,2, temperature 57° C. and agitation 100 turns per minute. Under these conditions after 98 hours of fermentation 12,3% final concentration of L(+)-lactate was achieved. The yield of L(+)-lactate from metabolised glucose was 95,5%.

The invention claimed is:

1. An isolated biologically pure culture of the microorganism *Bacillus coagulans* strain SIM-7 DSM 14043.

2. A method for the production of L(+)-lactate comprising:

inoculating and cultivating the *Bacillus coazulans* strain SLM-7 DSM 14043 of claim 1, at a temperature between 53–65° C., in fermentation medium which contains fermentable sugars and partially fermentable sugars, including dextrins and starch; and recovering L(+)-lactate.

3. The method according to claim 2, wherein the cultivating step is carried out at a temperature of 57° C.

4. The method according to claim 2, wherein the cultivating step is carried out without sterilization of equipment and media.

5. The method according to claim 2, wherein the flour of cereals is used as the source of fermentable sugars.

\* \* \* \* \*